(12) United States Patent
Tanaka et al.

(10) Patent No.: US 12,141,708 B2
(45) Date of Patent: Nov. 12, 2024

(54) TYPE ESTIMATION MODEL GENERATION SYSTEM AND TYPE ESTIMATION SYSTEM

(71) Applicant: NTT DOCOMO, INC., Chiyoda-ku (JP)

(72) Inventors: Shigeki Tanaka, Chiyoda-ku (JP); Yusuke Fukazawa, Chiyoda-ku (JP)

(73) Assignee: NTT DOCOMO, INC., Chiyoda-ku (JP)

( * ) Notice: Subject to any disclaimer, the term of this patent is extended or adjusted under 35 U.S.C. 154(b) by 467 days.

(21) Appl. No.: 17/624,454

(22) PCT Filed: Jun. 17, 2020

(86) PCT No.: PCT/JP2020/023774
§ 371 (c)(1),
(2) Date: Jan. 3, 2022

(87) PCT Pub. No.: WO2021/005982
PCT Pub. Date: Jan. 14, 2021

(65) Prior Publication Data
US 2022/0351050 A1    Nov. 3, 2022

(30) Foreign Application Priority Data
Jul. 5, 2019   (JP) ................. 2019-126364

(51) Int. Cl.
*G06N 5/022*   (2023.01)
*G10H 1/00*    (2006.01)

(52) U.S. Cl.
CPC ........... *G06N 5/022* (2013.01); *G10H 1/0008* (2013.01); *G10H 2210/036* (2013.01)

(58) Field of Classification Search
CPC . G06N 5/022; G10H 1/0008; G10H 2210/036
See application file for complete search history.

(56) References Cited

U.S. PATENT DOCUMENTS

| | | | |
|---|---|---|---|
| 2010/0125539 A1* | 5/2010 | Aucouturier | G06F 16/683 706/46 |
| 2013/0311163 A1* | 11/2013 | Somekh | G06N 20/00 703/21 |
| 2019/0288657 A1* | 9/2019 | Arunachalam | G06F 16/68 |

FOREIGN PATENT DOCUMENTS

JP    2011-209483 A    10/2011

OTHER PUBLICATIONS

International Preliminary Report on Patentability issued Jan. 20, 2022 in PCT/JP2020/023774 (submitting English translation only), 5 pages.

(Continued)

*Primary Examiner* — Austin Hicks
(74) *Attorney, Agent, or Firm* — Oblon, McClelland, Maier & Neustadt, L.L.P.

(57) ABSTRACT

A type estimation model generation system is a system that generates a type estimation model used for type estimation of estimating one of a plurality of types to which a user belongs, the system including: a learning data acquiring unit configured to acquire learning time series information that is information of a time series about a plurality of used musical pieces and learning type information representing types to which users who have used the plurality of musical pieces belong that are learning data used for machine learning; and a model generating unit configured to generate the type estimation model by performing machine learning using information based on the learning time series information as an input for the type estimation model in units of musical pieces in order of the time series and information based on the learning type information as an output of the type estimation model.

9 Claims, 16 Drawing Sheets

(56) References Cited

OTHER PUBLICATIONS

International Search Report mailed on Aug. 18, 2020 in PCT/JP2020/023774 filed on Jun. 17, 2020, 2 pages.

* cited by examiner

| MUSICAL PIECE ID | SINGER NAME | GENRE NAME | ... |
|---|---|---|---|
| 1 | SINGER A | J-POP | |
| 2 | SINGER A | BALLADE | |
| 3 | SINGER C | J-POP | |

(b)

| SINGER NAME | SINGER ID |
|---|---|
| SINGER A | 1 |
| SINGER B | 2 |
| SINGER C | 3 |

(c)

| MUSICAL PIECE ID | SINGER ID | GENRE ID | ... |
|---|---|---|---|
| 1 | 1 | 2 | |
| 2 | 1 | 1 | |
| 3 | 3 | 2 | |

| SINGER ID | CHARACTERISTIC 1 | CHARACTERISTIC 2 |
|---|---|---|
| 1 | 0.3 | 0.1 |
| 2 | 0.2 | 0.3 |
| 3 | 0.9 | 0.1 |

(b)

| MUSICAL PIECE ID | SINGER CHARACTERISTIC 1 | SINGER CHARACTERISTIC 2 | GENRE CHARACTERISTIC 1 | ... |
|---|---|---|---|---|
| 1 | 0.3 | 0.1 | 3 | |
| 2 | 0.3 | 0.1 | 1 | |
| 3 | 0.9 | 0.1 | 2 | |

Fig.4

| WORD | IMPORTANCE LEVEL |
|------|------------------|
| LIKE | 0.941308 |
| CAN BE | 0.186409 |
| TALK | 0.118623 |
| BECOME | 0.103391 |
| LAUGH | 0.076888 |

Fig.6

| TERMINAL ID | SINGING TIME | MUSICAL PIECE | MUSICAL PIECE ID |
|---|---|---|---|
| A1 | 2018-07-01 22:55 | AAA | 1 |
| A1 | 2018-07-01 22:58 | BBB | 2 |
| A1 | 2018-07-01 23:25 | CCC | 3 |
| A1 | 2018-07-01 23:28 | DDD | 4 |
| A2 | 2018-07-01 22:55 | EEE | 5 |

Fig.8

|  | FIRST MUSICAL PIECE INFORMATION | SECOND MUSICAL PIECE INFORMATION | THIRD MUSICAL PIECE INFORMATION | FOURTH MUSICAL PIECE INFORMATION |
|---|---|---|---|---|
| Y (NEXT MUSICAL PIECE) |  |  |  |  |
| X (IMMEDIATELY PRECEDING MUSICAL PIECE) | 0 | FIRST MUSICAL PIECE INFORMATION | SECOND MUSICAL PIECE INFORMATION | THIRD MUSICAL PIECE INFORMATION |

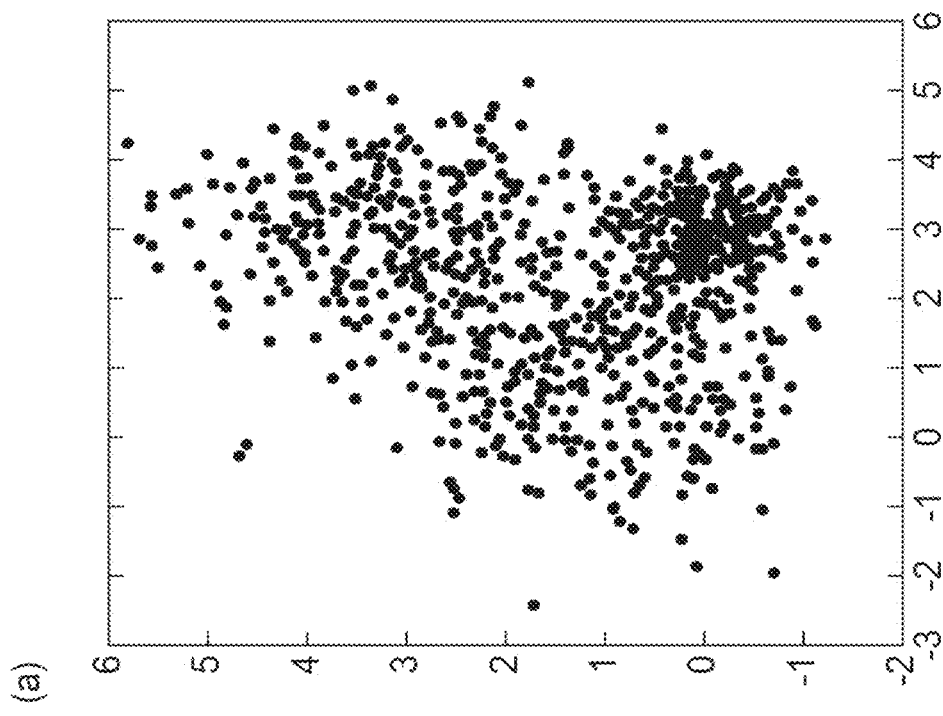
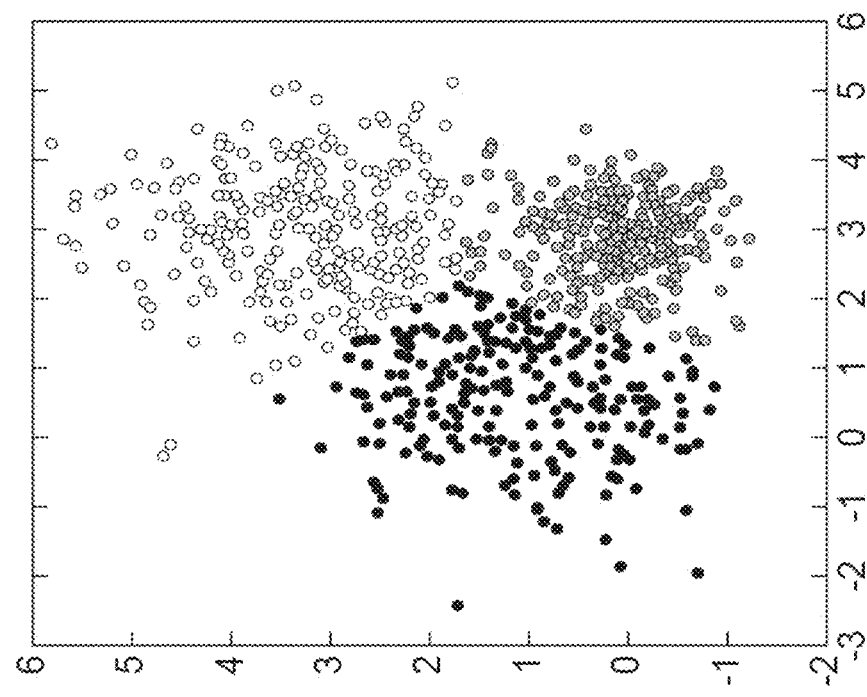
Fig.10

*Fig.11*

| SESSION | TYPE NUMBER |
|---------|-------------|
| A | 0 |
| B | 1 |

| Y OF SESSION A | 0 | 0 | 0 | 0 |
|---|---|---|---|---|
| X OF SESSION A | FIRST MUSICAL PIECE INFORMATION | SECOND MUSICAL PIECE INFORMATION | THIRD MUSICAL PIECE INFORMATION | FOURTH MUSICAL PIECE INFORMATION |

(b)

| Y OF SESSION B | 1 | 1 |
|---|---|---|
| X OF SESSION B | FIRST MUSICAL PIECE INFORMATION | SECOND MUSICAL PIECE INFORMATION |

TYPE ESTIMATION MODEL GENERATION SYSTEM AND TYPE ESTIMATION SYSTEM

TECHNICAL FIELD

The present invention relates to a type estimation model generation system generating a type estimation model used for type estimation of estimating one of a plurality of types to which a user belongs and a type estimation system estimating a type to which a user belongs using a type estimation model.

BACKGROUND ART

Conventionally, in order to provide an accurate service, clustering users of karaoke on the basis of singing histories of the users has been proposed (for example, see Patent Literature 1).

CITATION LIST

Patent Literature

[Patent Literature 1] Japanese Unexamined Patent Publication No. 2011-209483

SUMMARY OF INVENTION

Technical Problem

In the method disclosed in Patent Literature 1 described above, although users are clustered on the basis of singing histories, a sequence in which each user sang musical pieces is not appropriately taken into account. For example, in a case in which a user group formed of a plurality of users performs karaoke, generally, different users perform singing in a sequence, and thus a sequence of musical pieces that have been sung so far needs to be taken into account in clustering of the users (the user group). Thus, in the method disclosed in Patent Literature 1, there is a concern that clustering cannot be appropriately performed in view of this.

One embodiment of the present invention is in view of the situation described above, and an object thereof is to provide a type estimation model generation system and a type estimation system capable of appropriately classifying types of users on the basis of used musical pieces.

Solution to Problem

In order to achieve the object described above, according to one embodiment of the present invention, there is provided a type estimation model generation system that generates a type estimation model used for type estimation of estimating one of a plurality of types to which a user belongs, the type estimation model generation system including: a learning data acquiring unit configured to acquire learning time series information that is learning data used for machine learning and that is information of a time series about a plurality of used musical pieces and learning type information representing types to which users who have used the plurality of musical pieces belong; and a model generating unit configured to generate the type estimation model by performing machine learning using information based on the learning time series information acquired by the learning data acquiring unit as an input for the type estimation model in units of musical pieces in order of the time series and information based on the learning type information acquired by the learning data acquiring unit as an output of the type estimation model.

In addition, according to one embodiment of the present invention, there is provided a type estimation system that estimates a type to which a user belongs among a plurality of types using a type estimation model generated by a type estimation model generation system, the type estimation system including: a model use data acquiring unit configured to acquire type estimation time series information that is information of a time series about a plurality of used musical pieces; and a model using unit configured to estimate a type to which a user belongs by inputting information based on the type estimation time series information acquired by the model use data acquiring unit to the type estimation model in units of musical pieces in order of the time series.

According to one embodiment of the present invention, a type of a user can be estimated by using the time series information that is information of a time series about a plurality of musical pieces used by the user who is an estimation target of the type on the basis of the type estimation model generated using machine learning. The information based on the time series information is input to the type estimation model in units of musical pieces in order of the time series, and thus estimation of a type with the sequence of musical pieces that have been sung taken into account can be performed. Thus, according to one embodiment of the present invention, classification of types of users based on used musical pieces can be appropriately performed.

Advantageous Effects of Invention

According to one embodiment of the present invention, types of users can be appropriately classified on the basis of used musical pieces.

BRIEF DESCRIPTION OF DRAWINGS

FIG. 2 is a table illustrating an example of information about musical pieces and the like stored in the recommendation server.

FIG. 3 is a table illustrating an example of a characteristic quantity converted from each singer ID.

FIG. 4 is a table illustrating an example of importance levels of words included in lyrics of a musical piece.

FIG. 6 is a table illustrating an example of information of a time series representing musical pieces sung in the past.

FIG. 8 is a diagram illustrating an example of a correspondence relation of learning data used for generating a musical piece recommendation model.

FIG. 10 is a diagram illustrating an example of clustering performed for generating types of users.

FIG. 11 is a table illustrating an example of an identification number associated with each session.

FIG. 12 is a diagram illustrating an example of a correspondence relation of learning data used for generating a type estimation model.

DESCRIPTION OF EMBODIMENTS

Hereinafter, a type estimation model generation system and a type estimation system according to an embodiment of the present invention will be described in detail with reference to the drawings. In description of the drawings, the same reference signs will be assigned to the same elements, and duplicate description thereof will be omitted.

Figure 1:
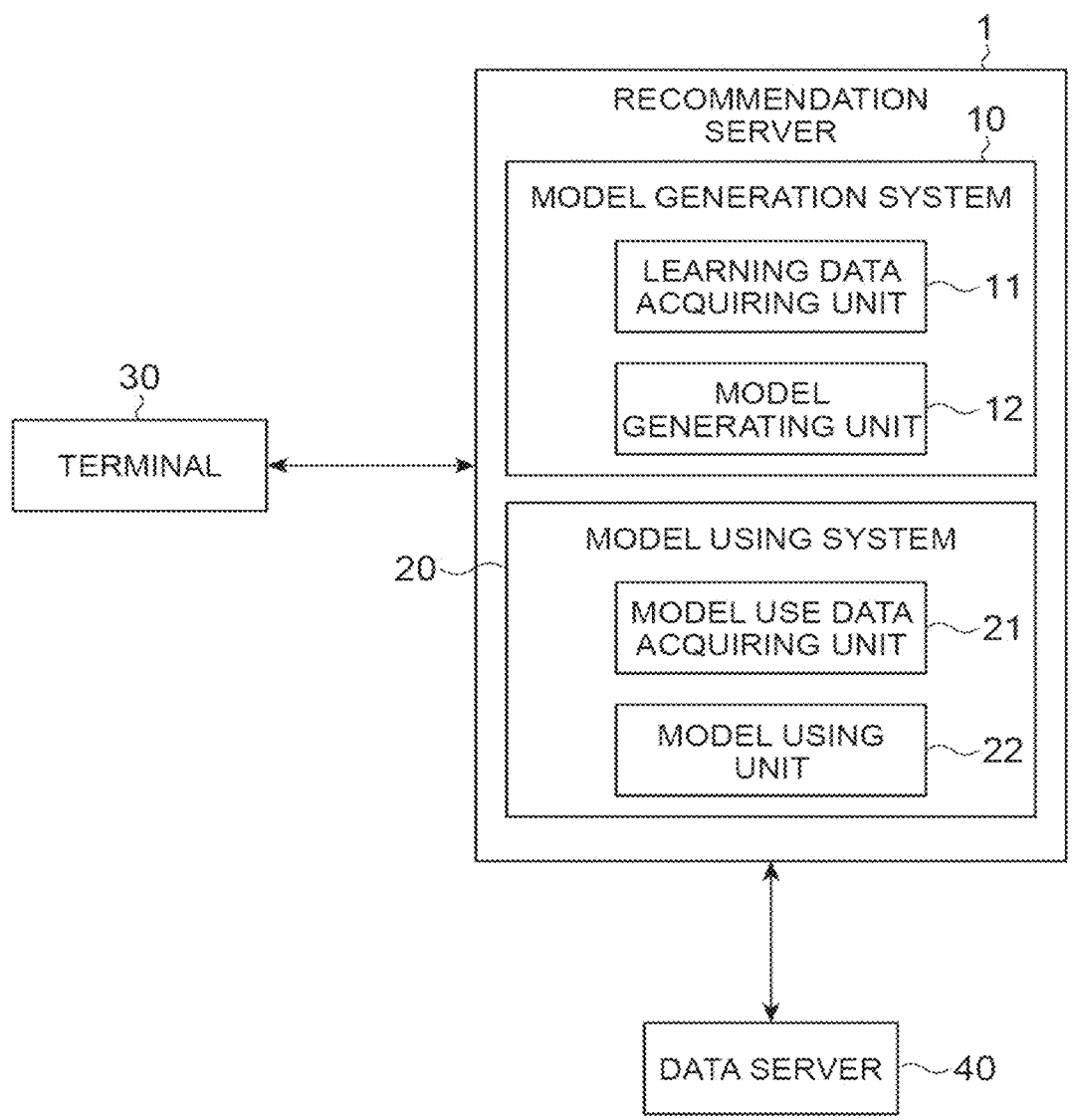
FIG. 1 is a diagram illustrating the configuration of a recommendation server that is a type estimation model generation system and a type estimation system according to an embodiment of the present invention.

FIG. 1 illustrates a recommendation server 1 that is a type estimation model generation system and a type estimation system according to this embodiment. The recommendation server 1 is a system that recommends information about a musical piece to a user. More specifically, the recommendation server 1 recommends a musical piece to sing or a singer thereof when a user sings karaoke. The recommendation server 1 recommends regarding a musical piece to sing first. In addition, the recommendation server 1 recommends regarding a musical piece to sing next after a musical piece is sung. The recommendation server 1 may recommend regarding a musical piece to sing next every time when a musical piece is being sung.

In this embodiment, a user who is a target for recommendation may include a group composed of a plurality of users performing karaoke at the same time, for example, a group of users singing songs in a sequence. In the following description, even in a case in which only a user is mentioned, it includes a group formed of a plurality of users. In addition, the recommendation server 1 may recommend information about a musical piece used by a user doing something other than karaoke. For example, the recommendation server 1 may perform recommendation of a musical piece for a user to listen to.

The recommendation server 1 generates a musical piece recommendation model (learned model) by performing machine learning and performs recommendation using the generated musical piece recommendation model. In addition, the recommendation server 1 performs type estimation of estimating one of a plurality of types to which a user belongs and uses a result of the type estimation for recommendation to the user. The type of user is a classification according to musical pieces sung by the user. The recommendation server 1 generates a type estimation model (learned model) by performing machine learning and performs type estimation using the generated type estimation model. The recommendation server 1 includes a model generation system 10 as a component for generating a musical piece recommendation model and a type estimation model and a model using system 20 as a component for performing recommendation and estimation of a type. The model generation system 10 is a type estimation model generation system according to this embodiment. The model using system 20 is a type estimation system according to this embodiment.

The recommendation server 1 is configured using a server apparatus having a communication function. The recommendation server 1 may be realized by a plurality of server apparatuses, in other words, computer systems. The recommendation server 1 can perform transmission/reception of information between the terminal 30 and the data server 40 through a network such as the Internet or a dedicated line. In addition, at the time of transmitting/receiving information, information may be relayed by a relay server disposed between such devices.

The terminal 30 is a terminal that is used by a user at a location such as a karaoke parlor. For example, the terminal 30 is used by a user to search for and input a musical piece at a location such as a karaoke parlor. For example, the terminal 30 is an information terminal that is provided at a location such as a karaoke parlor. Alternatively, the terminal 30 may be an information terminal such as a smartphone owned by an individual user. In such a case, an application for a karaoke parlor realizing the function of the terminal 30 is installed and used in the information terminal. The terminal 30 requests recommended content from the recommendation server 1, receives information about recommendation from the recommendation server 1, and performs output such as display. A user can determine a musical piece to sing by referring to the output.

The data server 40 is an apparatus that stores data used for recommendation using the recommendation server 1. The stored information will be described more specifically below. A plurality of data servers 40 may be provided for respective types of data.

Next, functions of the model generation system 10 and the model using system 20 included in the recommendation server 1 according to this embodiment will be described. As illustrated in FIG. 1, the model generation system 10 is configured to include a learning data acquiring unit 11 and a model generating unit 12.

The learning data acquiring unit 11 is a functional unit that acquires learning data used for machine learning generating a musical piece recommendation model. The learning data acquiring unit 11 acquires learning population information representing a population for each attribute (characteristic) of persons at a place at which a musical piece is used and learning use musical piece information relating to the musical piece as learning data. The learning data acquiring unit acquires learning population information representing a population for each attribute of persons and each time at a place at which a musical piece is used. Attributes of persons include at least one of occupations and preferences of persons.

In addition, the learning data acquiring unit 11 acquires learning time series information that is information of a time series about a plurality of used musical pieces used and learning use musical piece information about musical pieces used after the plurality of musical pieces as learning data. The learning data acquiring unit 11 acquires learning time series information including information relating to singers of used musical pieces. The learning data acquiring unit 11 acquires learning time series information including information relating to genres of used musical pieces. The learning data acquiring unit 11 acquires learning time series information including information relating to words included in lyrics of used musical pieces. The learning data acquiring unit 11 acquires learning time series information including information relating to audio data of used musical pieces. The learning data acquiring unit 11 acquires information including information that is information of a time series relating to a plurality of used musical pieces and that represents times at which respective musical pieces are used and generates learning time series information and learning use musical piece information on the basis of the times. The learning data acquiring unit 11 acquires learning type information that represents types to which users that have used the plurality of musical pieces belong. More specifically, the learning data acquiring unit 11 acquires learning data as below.

The learning data acquiring unit 11 stores information relating to musical pieces in advance. These musical pieces are musical pieces that can be provided in karaoke, in other words, musical pieces that can be used by a user. The learning data acquiring unit 11 stores a musical piece table illustrated in FIG. 2(a). In the musical piece table, a musical piece ID, a singer name, a genre name, and the like are stored in association with each other. The musical piece ID is information (an identifier) for identifying each musical piece set in advance. The singer name is a name of a singer singing the musical piece. The genre name is information that represents a genre of a corresponding musical piece. As illustrated in FIG. 2(a), examples of the genre name include "J-POP," "Ballade," and the like. Information stored in the recommendation server 1 in advance is acquired from the data server 40 or the like unless mentioned otherwise.

The learning data acquiring unit 11 stores a singer ID table illustrated in FIG. 2(b). In the musical piece table, a singer name and a singer ID are stored in association with each other. The singer ID is information (an identifier) for identifying each singer set in advance. The singer ID is set as a numerical value, for example, an integer illustrated in FIG. 2(b), such that it can be used for machine learning. The learning data acquiring unit 11 converts each singer name of the musical piece table illustrated in FIG. 2(a) into a singer ID on the basis of the association represented by the singer ID table illustrated in FIG. 2(b).

In addition, similar to singer names, also for genre names, the learning data acquiring unit 11 stores an ID table and converts each genre name of the musical piece table into a genre ID on the basis of the corresponding ID table. Similar to singer IDs, a genre ID is also set as a numerical value, for example, an integer, such that it can be used for machine learning. In this way, the learning data acquiring unit 11 generates a musical piece table using IDs (a musical piece table converted into IDs) illustrated in FIG. 2(c). The ID table may be generated by the recommendation server 1 instead of being acquired from the data server 40.

As will be described below, singer IDs are converted into characteristic quantities in the musical piece recommendation model. An example of the characteristic quantities is illustrated in FIG. 3(a). The characteristic quantities are numerical values of a dimension number set in advance. In the example illustrated in FIG. 3(a), two dimensional characteristic quantities are illustrated. The dimension number of characteristic quantities is generally a numerical value of several dimensions to several tens of dimensions. The characteristic quantities are updated at the time of machine learning and are substituted with better numerical values. Similar to the singer IDs, the genre IDs are converted into characteristic quantities as well. FIG. 3(b) illustrates a characteristic-quantized (converted into a characteristic quantity) musical piece table.

The learning data acquiring unit 11 acquires information representing lyrics of each musical piece from the data server 40. The learning data acquiring unit 11 divides the lyrics into words by performing morphological analysis. The learning data acquiring unit 11 calculates an importance level of each word with an appearance frequency of each word in the lyrics taken into account for each musical piece. Words of which importance levels are calculated may be set in advance. For example, importance levels of words that are verbs, adjectives, and adjective verbs may be calculated. The learning data acquiring unit 11 calculates an importance level $tfidf(t_i, d_j)$ of a word $t_i$ in a musical piece (lyrics) $d_j$ using the following equation.

$$idf(t_i) = \log(\text{total number of musical pieces/number of musical pieces in which word } t_i \text{ appears}) = \log(N/df(t_i))$$

$$tf(t_i, d_j) = \text{number of times of appearance of word } t_i \text{ in musical piece } d_j/\text{sum of numbers of appearances of all words of musical piece } d_j = f(t_i, d_j)/\Sigma_{t_k \in d_j} f(t_k, d_j)$$

$$tfidf(t_i, d_j) = tf(t_i, d_j) \cdot idf(t_i)$$

The importance levels of words in a certain musical piece are illustrated in FIG. 4. As information based on lyrics of a musical piece, arbitrarily characteristic-quantized information other than the importance levels of words may be used.

Figure 5:
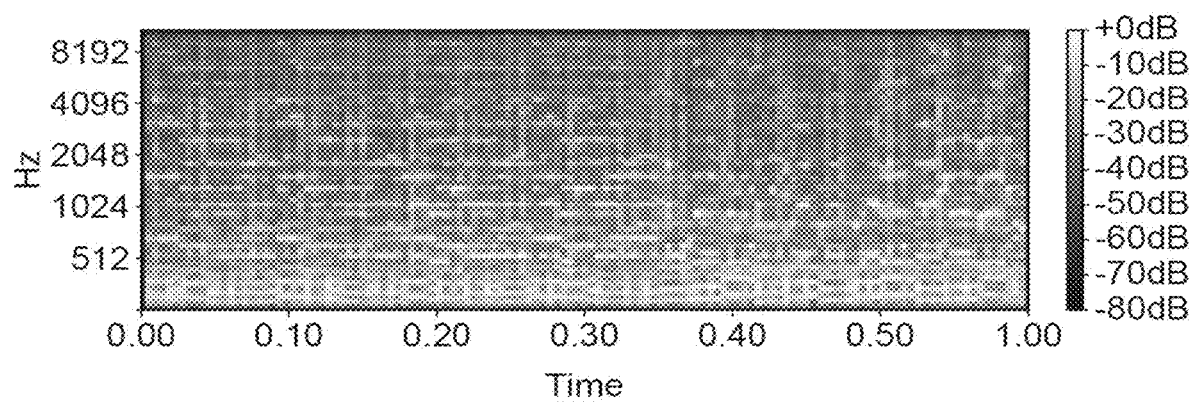
FIG. 5 is a diagram illustrating an example of a spectrogram converted from audio data of a musical piece.

The learning data acquiring unit 11 acquires audio data of each musical piece from the data server 40. For example, the audio data is data (a sound source) used for playback of a musical piece in karaoke and is data of an audio waveform that is a numerical value of a signal intensity for each time. As the audio data, MPEG-1 Audio Layer-3 (MP3) may be used. The learning data acquiring unit 11 converts audio data of each musical piece into a spectrogram (mel spectrogram). The learning data acquiring unit 11 converts audio data of a time frame set to be common in advance into a spectrogram for each musical piece. For example, audio data for one minute from the beginning of each musical piece is converted into a spectrogram. The reason for this is that musical pieces having different time lengths are handled as data of the same size. The conversion of audio data into a spectrogram can be performed using a conventional method. The converted spectrogram is data of a numerical value of a signal intensity (for example, dB) for each time (for example, seconds elapsed from the beginning of a musical piece) and each frequency (for example, Hz). FIG. 5 illustrates an example of a spectrogram of a certain musical piece. As illustrated in FIG. 5, a spectrogram can be handled as an image. In addition, as the information based on audio data, arbitrarily characteristic-quantized information other than the spectrogram may be used. Furthermore, as the information based on audio data, the data of the waveform described above may be used.

The learning data acquiring unit 11 stores information representing a population for each place and each attribute of persons in advance. For example, the learning data acquiring unit 11 stores information of a population for each mesh having four sides of 500 m set in advance for each hour. The attributes of persons are attributes that can have influence on choice of a musical piece in karaoke and are occupations and preferences of the persons. Classifications of occupations are "company employee," "self-employed," "student," "full-time housewife (husband)," "unemployed," and the like. Classifications of preferences are hobbies preferred by users such as "shopping" and "animation." The information described above is information representing a population of the number of occupations×the number of preferences for each mesh and each hour. As the attributes, only any one of the occupation and the preference may be used. In addition, other attributes that can have influence on choice of a musical piece in karaoke, for example, attributes such as sex, age, and the like, may be used. The information of a population for each of the attributes describe above, for example, can be generated as space statistical information from information representing locations of mobile phones and information registered for subscribers of the mobile phones.

The learning data acquiring unit 11 acquires information of a time series about a plurality of musical pieces used in the past. More specifically, the learning data acquiring unit 11 acquires a log that is information of a time series representing a plurality of musical pieces sung in the past at a location such as a karaoke parlor. The learning data acquiring unit 11 acquires the information from the data server 40. FIG. 6 illustrates an example of the information. The information is information in which a terminal ID, a singing time, a musical piece, and a musical piece ID are associated with each other. The terminal ID is information (an identifier) for identifying the terminal 30 used in the use of a musical piece at a location such as a karaoke parlor. A terminal ID is set for each terminal 30 in advance. The singing time is information representing a time at which the musical piece is used (sung) (for example, as illustrated in FIG. 6, year/month/date hour:minute). The musical piece is a musical piece name of the used (sung) musical piece. The musical piece ID is a musical piece ID of a used (sung) musical piece.

At a location such as a karaoke parlor, users do not usually log in when using the terminal 30. For this reason, like the information illustrated in this embodiment, there are cases in which information representing a user who sang each musical piece is not included in the singing history at a location such as a karaoke parlor. For machine learning, information of a history relating to the use of musical pieces needs to be configured in units of respective users. The learning data acquiring unit 11 generates learning time series information and learning use musical piece information as information used for machine learning on the basis of the singing times included in the acquired information. In this embodiment, one session is set from user's start to end of karaoke, for example, from entering a location such as a karaoke parlor to leaving the location. The learning data acquiring unit 11 generates the information described above in units of respective sessions.

The learning data acquiring unit 11 refers to a singing time of information of a musical piece that has been sung immediately before with the same terminal ID for each piece of the acquired information. The learning data acquiring unit 11 determines whether or not a predetermined time set in advance has elapsed from singing of the immediately preceding musical piece. When the predetermined time has not elapsed, it is assumed that singing is performed by the same user, and the learning data acquiring unit 11 determines that the corresponding information is information configuring the same session as that of the information of the immediately preceding musical piece. When the predetermined time has elapsed, it is assumed that singing is performed by another user, and the learning data acquiring unit 11 determines that the corresponding information is information configuring another session different from that of the information of the immediately preceding musical piece. For example, in the example of information illustrated in FIG. 6, information of a first row and a second row configures one session, information of a third row and a fourth row configures one session, and information of a fifth row configures one session.

Figure 7:
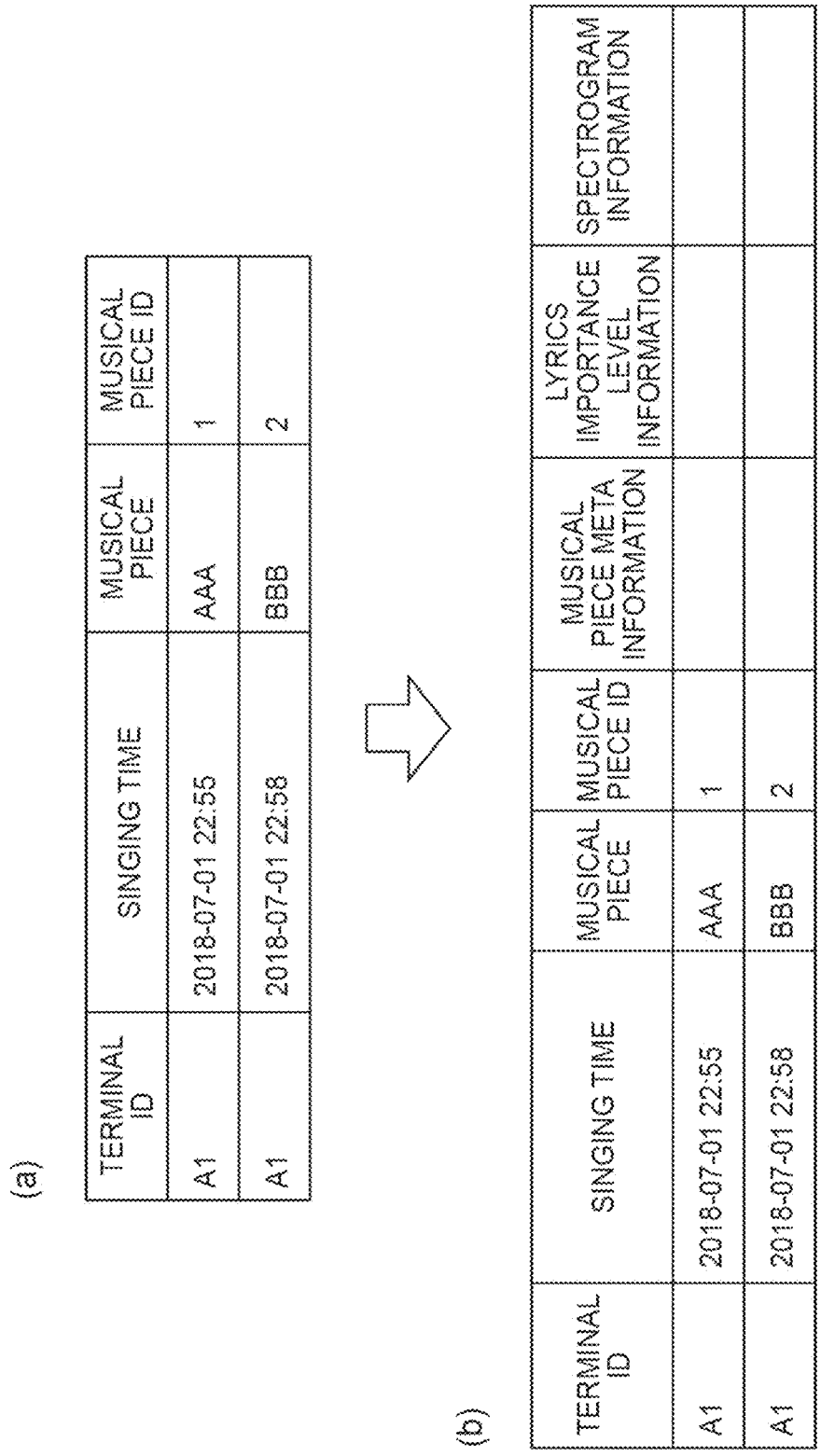
FIG. 7 is a table illustrating an example of learning data used for generating a musical piece recommendation model.

The learning data acquiring unit 11 associates each piece of the information about musical pieces described above with each piece of information of a musical piece sung in each session by using the musical piece ID as a key. More specifically, musical piece meta information including a singer ID and a genre ID illustrated in FIG. 2(*c*), lyric importance level information illustrated in FIG. 4, and spectrogram information illustrated in FIG. 5 are associated (combined). FIG. 7(*a*) illustrates information before each piece of information about musical pieces in a certain session is associated therewith, and FIG. 7(*b*) illustrates information after each piece of information about musical pieces in a certain session is associated.

Subsequently, the learning data acquiring unit 11 generates learning time series information and learning use musical piece information on the basis of the information described above. The learning data acquiring unit 11 sets musical pieces represented in each piece of information of the session to a first musical piece, a second musical piece, . . . in order of singing times. The learning data acquiring unit 11 sets the musical pieces in the sequence described above in the session as musical pieces corresponding to outputs (Y) of the musical piece recommendation model at the time of machine learning. Information about the musical piece is learning use musical piece information. In the information about musical pieces, a musical piece ID and a singer ID are regarded as learning use musical piece information. The learning data acquiring unit 11 converts information representing a musical piece ID and a singer ID in the learning use musical piece information into a vector of dimensions corresponding to the number of the kinds of IDs in which elements corresponding to an ID is set to 1, and the other elements are set to 0. The conversion described above is not performed for the learning time series information, and the learning time series information is handled as information of numerical values.

The learning data acquiring unit 11 sets a musical piece immediately before a musical piece relating to the learning use musical piece information in the session as a musical piece corresponding to an input (X) to the musical piece recommendation model at the time of machine learning. The information about the musical piece is the learning time series information. In the information about the musical piece, all the information except for a terminal ID, a singing time, a musical piece, and a musical piece ID illustrated in FIG. 7(*b*) is regarded as the learning time series information. An example of a correspondence relation between the learning time series information and the learning use musical piece information is illustrated in FIG. 8. There is no musical piece of an input corresponding to the first musical piece of an output. Information of an input corresponding to the first musical piece of the output (information "0" of X (the immediately preceding musical piece) in FIG. 8) is information set to a numerical value (for example, 0) indicating that there is no corresponding musical piece in all the information except for the terminal ID, the singing time, the musical piece, and the musical piece ID illustrated in FIG. 7(*b*).

The learning data acquiring unit 11 acquires information representing a place corresponding to each session. The place corresponding to each session is a place at which the terminal 30 used when singing relating to the session is performed is located. The learning data acquiring unit 11 acquires information representing a mesh in which the place is present as information representing the place. For example, in a case in which a terminal 30 is provided at a location such as a karaoke parlor, the learning data acquiring unit 11 stores a correspondence relation between a terminal ID of the terminal 30 and a mesh in which the terminal 30 is provided in advance and acquires information representing the mesh on the basis of the correspondence relation from the terminal ID represented in information relating to the session. In addition, in a case in which a terminal 30 is held by a user, the learning data acquiring unit 11 stores a correspondence relation between a location and a mesh including a location in advance, acquires location information (for example, information of longitude and latitude) representing the location of the terminal 30 together with information about a session, and acquires information representing a mesh on the basis of the correspondence relation from the location information. In this case, location information is transmitted from a terminal 30 in advance when karaoke is used from the terminal 30 and is stored in the data server 40 together with the information about the session.

The learning data acquiring unit 11 acquires information representing a population of the mesh from the acquired information representing the mesh (reads the information from information stored therein). In addition, the learning data acquiring unit 11 may acquire information representing a population according a time relating to the session. For example, the learning data acquiring unit 11 may acquire information of a population of a time frame including a singing time of a first musical piece of the session. The acquired information representing a population is learning population information used as an input to the musical piece recommendation model at the time of machine learning.

The learning data acquiring unit 11 acquires the learning population information, the learning time series information, and the learning use musical piece information for the number of sessions that are sufficient for generating the musical piece recommendation model. In other words, such information for sessions that are sufficient for the musical piece recommendation model is prepared in advance.

In addition, the learning data acquiring unit 11 is a functional unit that acquires learning data used for machine learning generating a type estimation model. The learning data acquiring unit 11 acquires learning time series information that is information of a time series relating to a plurality of musical pieces used and learning type information representing types to which users using the plurality of musical pieces belong as learning data. The learning data acquiring unit 11 acquires the learning time series information including information about singers of used musical pieces. The learning data acquiring unit 11 acquires the learning time series information including information about genres of the used musical pieces. The learning data acquiring unit 11 acquires the learning time series information including information about words included in lyrics of the used musical pieces. The learning data acquiring unit 11 acquires the learning time series information including information about audio data of the used musical pieces. The learning data acquiring unit 11 acquires information that is information of a time series relating to a plurality of used musical pieces and includes information representing times at which musical pieces are used and generates learning time series information and learning use musical piece information on the basis of the times. The learning data acquiring unit 11 acquires learning time series information for each of a plurality of users, generates a plurality of types of estimation targets by performing clustering of the acquired learning time series information, and acquires learning type information on the basis of the generated types. In addition, the types generated here are pseudo types that are generated through the clustering process. More specifically, the learning data acquiring unit 11 acquires learning data as below. In the acquisition of learning data described below, each session is handled as corresponding to each user.

Figure 9:
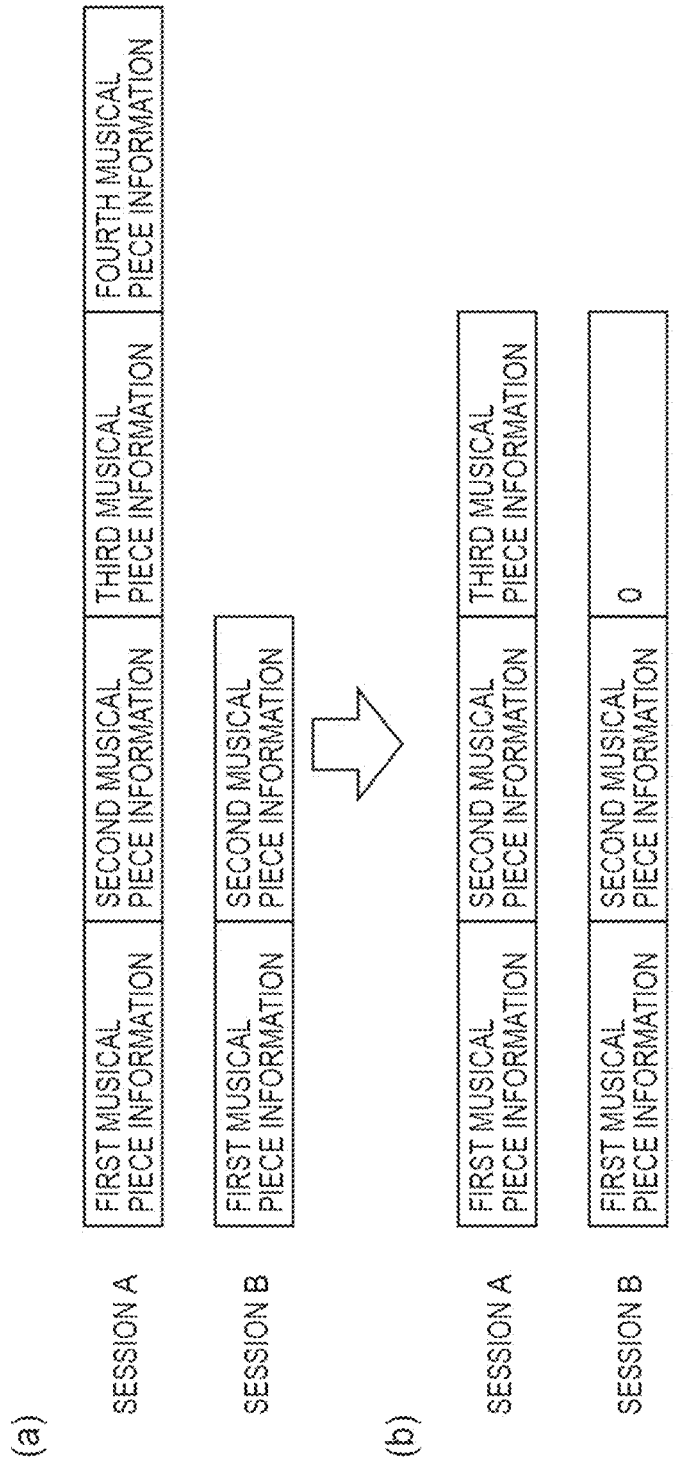
FIG. 9 is a diagram illustrating an example of learning data used for generating a type estimation model.

The learning data acquiring unit 11 generates learning time series information from information in which information about a musical piece is associated with each piece of information of musical pieces sung in each session (information of which an example is illustrated in FIG. 7) which has been used for generation of learning data for generating a musical piece recommendation model. The learning data acquiring unit 11 sets musical pieces represented in each piece of information of a session to a first musical piece, a second musical piece, . . . in order of singing times. The learning data acquiring unit 11 sets information about musical pieces in a sequence described above in the session as musical pieces corresponding to the learning time series information. In the information about the musical pieces, all information except for a terminal ID, a singing time, a musical piece, and a musical piece ID illustrated in FIG. 7(*b*) is set as learning time series information. FIG. 9(*a*) illustrates an example of learning time series information for two sessions (session A and session B). This information is acquired by excluding information "0" from the learning time series information used for generating a musical piece recommendation model represented in X (immediately preceding pieces) in FIG. 8.

In addition, the learning data acquiring unit 11 acquires learning type information as below. The learning data acquiring unit 11 generates a plurality of types that are estimation targets by performing clustering of the learning time series information and acquires learning type information on the basis of the generated types. The learning data acquiring unit 11 sets the lengths of data of all the sessions to be constant. For example, the lengths are set to a length of information about musical pieces corresponding to a number set in advance (for example, three musical pieces). Information of which the data length is set to be constant is illustrated in FIG. 9(*b*).

For example, as in the session A illustrated in FIG. 9(*a*), in a case in which the learning time series information includes information about four or more musical pieces, only information about the first to third musical pieces is used for clustering. In addition, as in the session B illustrated in FIG. 9(*a*), in a case in which the learning time series information includes information about only two or fewer musical pieces, information corresponding to insufficient musical pieces is newly added. The newly added information (information "0" of the session B illustrated in FIG. 9(*b*)) is information set to a numerical value (for example, 0) indicating that the musical piece is not present for all the information except for a terminal ID, a singing time, a musical piece, and a musical piece ID illustrated in FIG. 7(*b*). In other words, in this case, the rear side of the learning time series information is filled with zeros. In addition, in the information used at the time of clustering, information of which a numerical value represents an ID such as a singer ID and a genre ID is converted into a vector of dimensions corresponding to the number of the types of ID in which elements corresponding to IDs are set to 1, and other elements are set to 0. In addition, the conversion described above is not performed for the learning time series information used for machine learning, and the learning time series information is handled as information of a numerical value.

Figure 11:
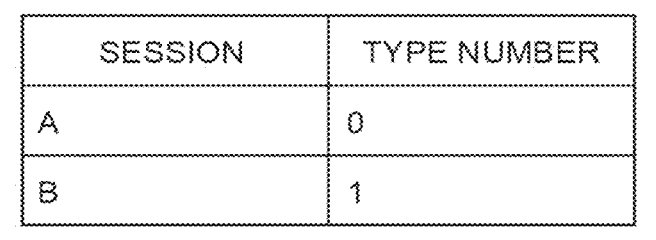

The learning data acquiring unit 11 performs clustering of the information of a session for clustering as illustrated in FIG. 10. FIG. 10(*a*) is a diagram schematically illustrating information of each session before clustering. One point corresponds to one session. FIG. 10(*b*) illustrates information of sessions of clustering. Sessions plotted using the same points represent that the sessions belong to the same cluster. As described above, all the information of sessions for clustering is a vector composed of numerical values of the same dimension (for example, information of musical pieces corresponding to three musical pieces), and thus clustering similar to a conventional method can be performed. For example, clustering can be performed using K-means clustering. Clusters generated by clustering are types (cluster types) to which users belong. The learning data acquiring unit 11 assigns identification numbers (cluster numbers) to types and, as illustrated in FIG. 11, associates an identification number of a type to which each session belongs with the session.

The learning data acquiring unit 11 sets information of identification numbers of types in a session that corresponds to the number of musical pieces included in the session as information that is an output (Y) of the type estimation model at the time of machine learning. This information is the learning type information. The learning data acquiring unit 11 converts identification numbers of types in the learning type information into a vector of dimensions corresponding to the number of types of identification numbers in which elements corresponding to identification numbers are set to 1, and other elements are set to 0. The learning data acquiring unit 11 sets the learning time series information in a session as information that is an input (X) to the type estimation model at the time of machine learning. An example of a corresponding relation between the learning time series information and the learning type information is illustrated in FIGS. 12(*a*) and 12(*b*). As illustrated in FIGS. 12(*a*) and 12(*b*), information about one musical piece and information of one identification number are associated with each other.

Similar to the information for generation of a musical piece recommendation model, the learning data acquiring unit 11 acquires learning time series information and learning type information of sessions corresponding to a number sufficient for generation of a type estimation model. In addition, the learning data acquiring unit 11 may acquire the learning time series information and the learning type information using a method other than that described above. The learning data acquiring unit 11 outputs the acquired learning data to the model generating unit 12.

Figure 13:
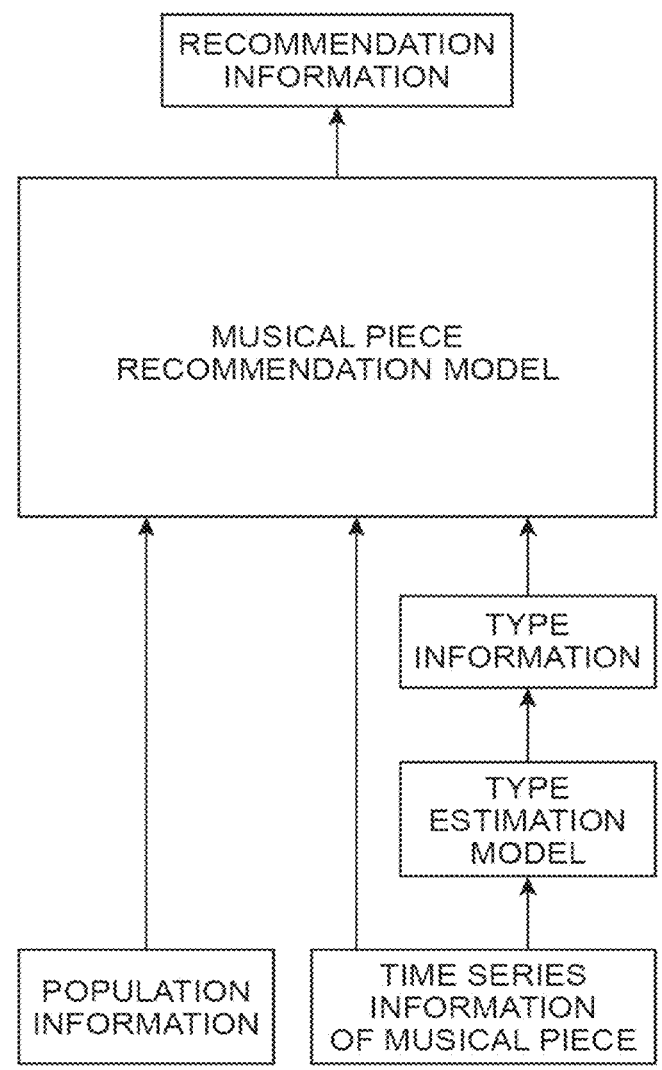
FIG. 13 is a diagram schematically illustrating a method of using a musical piece recommendation model and a type estimation model.

The model generating unit 12 is a functional unit that generates a musical piece recommendation model by performing machine learning using the learning data acquired by the learning data acquiring unit 11. In addition, the model generating unit 12 generates a type estimation model by performing machine learning using the learning data acquired by the learning data acquiring unit 11. FIG. 13 schematically illustrates a method used for the musical piece recommendation model and the type estimation model generated by the model generating unit 12.

In order to generate a musical piece recommendation model, the model generating unit 12 performs machine learning using information based on the learning population information acquired by the learning data acquiring unit 11 as an input to the musical piece recommendation model and information based on the learning use musical piece information acquired by the learning data acquiring unit 11 as an output of the musical piece recommendation model. In order to generate a musical piece recommendation model, the model generating unit 12 performs machine learning using information based on the learning time series information acquired by the learning data acquiring unit 11 as an input to the musical piece recommendation model in units of musical pieces in order of time series and information based on the learning use musical piece information acquired by the learning data acquiring unit 11 as an output of the musical piece recommendation model. In order to generate a musical piece recommendation model, the model generating unit 12 performs machine learning using also the information based on the learning type information acquired by the learning data acquiring unit 11 as an input to the musical piece recommendation model.

As illustrated in FIG. 13, the musical piece recommendation model generated by the model generating unit 12 is a model that receives information based on recommendation population information representing a population for each attribute of persons at a place at which a musical piece is used (population information illustrated in FIG. 13), recommendation time series information that is information of a time series about a plurality of used musical pieces (time series information of musical pieces illustrated in FIG. 13), and recommendation type information representing a type to which a user belongs (type information illustrated in FIG. 13) as inputs and outputs information about a musical piece to recommend (recommendation information illustrated in FIG. 13). In other words, the musical piece recommendation model is a model that predicts information about a musical piece to recommend that is Y from the population information, the type information, and the time series information of musical pieces that is X illustrated in FIG. 8. For example, the musical piece recommendation model is configured to include a neural network. The neural network may be a network of a multiple layers. In other words, the model generating unit 12 may generate a musical piece recommendation model by performing deep learning.

For example, in the musical piece recommendation model, neurons corresponding to the number of dimensions of the population information are provided in an input layer as neurons used for inputting the population information. More specifically, as described above, neurons corresponding to the number of occupations x the number of preferences are provided.

In addition, for example, in the musical piece recommendation model, neurons corresponding to the number of dimensions of information about one musical piece are provided in the input layer as neurons for inputting information about musical pieces. More specifically, as described above, neurons corresponding to the number of dimensions of the musical piece meta information, the lyrics importance level information, and the spectrogram information are provided. The musical piece recommendation model receives information about a plurality of musical pieces of a time series in order of the musical pieces of the time series as an input. In addition, information indicating that there is no sung musical piece before the input of the information about sung musical pieces is input to the musical piece recommendation model. The information is information corresponding to the musical piece meta information, the lyrics importance level information, and the spectrogram information in which all the numerical values are set to 0 and is information similar to the information "0" of X (the immediately preceding musical piece) illustrated in FIG. 8.

By inputting the information, the musical piece recommendation model can output information about a musical piece to recommend even in a state in which no musical piece has been sung by a user.

In addition, for example, in the musical piece recommendation model, neurons corresponding to the number of dimensions of the number of the type information (for example, the number of types) are provided in the input layer as neurons used for inputting type information. As will be described below, similar to the information about musical pieces, also the type information is information of a time series, and thus the musical piece recommendation model receives type information of a time series as an input.

For example, the musical piece recommendation model outputs a numerical value representing a degree of recommendation for each musical piece and a numerical value representing a degree of recommendation for a singer as information about musical pieces to recommend. In an output layer of the musical piece recommendation model, neurons corresponding to the number of musical pieces that are recommendation targets are provided as neurons used for outputting numerical values representing degrees of recommendation for musical pieces. In machine learning, in a case in which a vector in which elements of sung musical pieces are set to 1, and elements of the other musical pieces are set to 0 is used as learning use musical piece information, as an output numerical value becomes larger, it represents that the degree of recommendation becomes higher. In the output layer of the musical piece recommendation model, neurons corresponding to the number of singers that are recommendation targets are provided as neurons used for outputting numerical values representing degrees of recommendation of singers. In machine learning, in a case in which a vector in which elements of singers of sung musical pieces are set to 1, and elements of the other singers are set to 0 is used as learning use musical piece information, as an output numerical value becomes larger, it represents that the degree of recommendation becomes higher.

The musical piece recommendation model outputs information about a musical piece to recommend every time when the information about a musical piece is input. Information about a musical piece to recommend, which is output, is information about a musical piece to recommend after the musical piece relating to the input information. First, when information indicating that there is no musical piece that has been previously sung is input, the musical piece recommendation model outputs information about a musical piece to recommend as a first musical piece. Next, when information about a musical piece that has been sung as the first musical piece is input, the musical piece recommendation model outputs information about a musical piece to recommend as a second musical piece. In this way, the musical piece recommendation model sequentially outputs information about a musical piece to recommend next in accordance with sequential inputs of information about a musical piece that has been sung.

In addition, the musical piece recommendation model generated by the model generating unit 12 may be configured by a model other than the neural network.

The model generating unit 12 receives learning data from the learning data acquiring unit 11 as an input. The model generating unit 12 generates a musical piece recommendation model by performing machine learning using numerical values represented by the learning time series information that is information relating to musical pieces of a time series, the learning population information, and the learning type information in the input learning data as input values for the musical piece recommendation model and using the learning use musical piece information as an output value of the musical piece recommendation model. The learning time series information and the learning type information are set as input values for the musical piece recommendation model in units of musical pieces in order of the time series of the session. In addition, first information in the learning type information (information corresponding to the information indicating that no musical piece is present that is first information in the learning time series information) is set to information representing none of the types (for example, information in which elements corresponding to all the types are set to 0).

In addition, the learning use musical piece information is set as an output value of the musical piece recommendation model in units of musical pieces in order of the time series of the session. At that time, as a correspondence relation is illustrated in FIG. 8, predetermined learning time series information and learning type information are set as input values, learning use musical piece information corresponding to such information is set as an output value. In other words, information of a musical piece to be recommend next is output on the basis of a history of musical pieces sung in the session.

A singer ID that is input to the musical piece recommendation model as one numerical value is converted into a characteristic quantity that is a numerical value of a dimension number set in advance as illustrated in FIG. 3(a). When machine learning of the musical piece recommendation model starts, the model generating unit 12 gives a random numerical value as an initial value of the characteristic quantity. In the musical piece recommendation model, the characteristic quantity after conversion is used for generation of an output value. By performing the conversion into the characteristic quantity, an ID as a numerical value can be appropriately handled in the musical piece recommendation model, and an appropriate output value can be acquired. Similar to the singer ID, a genre ID is also converted into a characteristic quantity. In addition, also the learning population information may be converted into a characteristic quantity. Furthermore, conversion of each piece of information into a characteristic quantity may not be performed in the musical piece recommendation model.

As described above, the learning time series information and the learning type information are sequentially input to the musical piece recommendation model in units of musical pieces. In order to handle the information as information of a time series in the musical piece recommendation model, a gated recurrent unit (GRU) is used inside the musical piece recommendation model.

The machine learning described above can be performed similar to the method of conventional machine learning. The model generating unit 12 outputs the generated musical piece recommendation model to the model using system 20.

In order to generate a type estimation model, the model generating unit 12 performs machine learning using information based on the learning time series information acquired by the learning data acquiring unit 11 as inputs to the type estimation model in units of musical pieces in order of the time series and using information based on the learning type information acquired by the learning data acquiring unit 11 as an output of the type estimation model.

As illustrated in FIG. 13, a type estimation model generated by the model generating unit 12 is a model that receives information based on type estimation time series information (time series information of musical pieces illustrated in FIG. 13) that is information of a time series relating to a plurality of musical pieces used by a user as an input and outputs information about an estimated type to which the user belongs (the type information illustrated in FIG. 13). In other words, the type estimation model is a model that predicts type information that is Y from time series information of a musical piece that is X illustrated in FIGS. 12(a) and 12(b). The type estimation model, for example, is configured to include a neural network. The neural network may be a network of multiple layers. In other words, the model generating unit 12 may generate a type estimation model by performing deep learning.

For example, in the type estimation model, neurons corresponding to a dimension number of information about one musical piece are provided in the input layer as neurons used for inputting information about a musical piece. The neurons are similar to neurons used for inputting information about a musical piece to the musical piece recommendation model except for the following points. In the type estimation model, different from the musical piece recommendation model, learning and estimation (prediction) are not performed in a state in which no musical piece has been sung by a user.

For example, the type estimation model outputs a numerical value representing a degree of a user belonging to each type as information about a type to be estimated. In the type estimation model, neurons corresponding to the number of types are provided in the output layer as neurons for outputting numerical values representing degrees of the user belonging the types. In machine learning, in a case in which a vector in which an element of an identification number of the type to which a user belongs is set to 1, and the other elements of the musical piece are set to 0 is used as the learning type information, when the output numerical value becomes larger, it represents that a degree of the user belonging to the type is higher.

The type estimation model outputs information about a type every time when information about a musical piece is input. The output information about a type is information about a type that is estimated using musical pieces of a time series relating to the input information. First, when information about a musical piece that has been sung as a first musical piece is input, the type estimation model outputs information about a type estimated from the information. Subsequently, when information about a musical piece that has been sung as a second musical piece is input, the type estimation model outputs information of a type estimated from information until now (information of the first musical piece and the second musical piece). In this way, the type estimation model sequentially outputs information about an estimated type in accordance with sequential inputs of information about a musical piece that has been sung. In addition, in accordance with sequential inputs of information about a musical piece that has been sung, a degree of a user belonging to each type can be changed as well.

The information about a type output by the type estimation model is input to the musical piece recommendation model as illustrated in FIG. 13 at the time of recommending a musical piece to a user.

In addition, the type estimation model generated by the model generating unit 12 may be configured by a model other than the neural networks as described above.

The model generating unit 12 generates a type estimation model by performing machine learning using numerical values represented by the learning time series information that is information about musical pieces of a time series in the input learning data as input values for the type estimation model and the type information as an output value of the type estimation model. The learning time series information is set to an input value for the type estimation model in units of musical pieces in order of the time series of the session.

In addition, the type information is set as an output value of the type estimation model in units corresponding to the units of the learning time series information in order of the time series as illustrated in FIG. 12. At that time, as a correspondence relation is illustrated in FIG. 12, when predetermined learning time series information is set as an input value, type information corresponding to the information is set as an output value. In other words, information of a type estimated from a history of musical pieces that have been sung in the session is configured to be output.

As described above, the learning time series information is sequentially input to the type estimation model in units of musical pieces. In order to handle the information as information of a time series in the type estimation model, a GRU is used inside the type estimation model.

The machine learning described above can be performed similar to the method of conventional machine learning. The model generating unit 12 outputs the generated type estimation model to the model using system 20. For example, the processes performed by the learning data acquiring unit 11 and the model generating unit 12 may be performed as a daily batch process. The functions of the model generation system 10 according to this embodiment have been described as above.

Subsequently, the function of the model using system 20 according to this embodiment will be described. As illustrated in FIG. 1, the model using system 20 is configured to include a model use data acquiring unit 21 and a model using unit 22.

The model use data acquiring unit 21 is a functional unit that acquires model use data used for the musical piece recommendation model and the type estimation model. The model use data acquiring unit 21 acquires recommendation population information representing a population for each attribute of persons at a place at which musical pieces are used as the model use data. The model use data acquiring unit 21 acquires recommendation time series information that is information of a time series about a plurality of musical pieces used as the model use data. The model use data acquiring unit 21 acquires type estimation time series information that is information of a time series about a plurality of musical pieces used as the model use data.

The model use data acquiring unit 21 acquires data at the time when a user performs karaoke at a location such as a karaoke parlor, in other words, when a musical piece is used. When a user performs karaoke, a recommended content is requested for the recommendation server 1 from the terminal 30 used by the user. First, the request of the recommended content is performed before a user registers a musical piece to sing.

The model use data acquiring unit 21 acquires information representing a place at which karaoke is performed. For example, the model use data acquiring unit 21 acquires information representing a mesh in which the place is present as information representing the place. A terminal ID of the terminal 30 or location information (for example, information of longitude and latitude) representing the location of the terminal 30 is included in the request of the recommended content, and the model use data acquiring unit 21 acquires information representing a mesh from the terminal ID or the location information of the terminal 30 similar to the method used by the learning data acquiring unit 11. Similar to the method used by the learning data acquiring unit 11, the model use data acquiring unit 21 acquires information representing a population of the mesh from the acquired information representing the mesh as the recommendation population information (reads the information from information stored therein). In addition, in a case in which the stored population information is information for each time frame, population information associated with a time of the current time point is acquired.

When a user starts karaoke and sings a musical piece, the terminal 30 includes information representing the musical piece sung by the user in a request for a recommended content and transmits the request to the recommendation server 1. For example, the transmitted information is information represented in each row illustrated in FIG. 6. Information about a plurality of musical pieces (for example, nearest N logs) may be included in the transmitted information. The model use data acquiring unit 21 receives the information transmitted from the terminal 30. The model use data acquiring unit 21, as illustrated in FIG. 7, associates each piece of information about a musical piece with the information of a musical piece received from the terminal 30 by using the musical piece ID as a key. The associated information is the musical piece meta information, the lyrics importance level information, and the spectrogram information. The association is performed similar to the method used by the learning data acquiring unit 11.

The model use data acquiring unit 21 sequentially receives the transmitted information from the terminal 30 and performs the association described above. In addition, the model use data acquiring unit 21 may determine whether information relating to each musical piece acquired similar to the method used by the learning data acquiring unit 11 configures the same session as that of information about another musical piece. The model use data acquiring unit 21 generates information about musical pieces of a time series for each session on the basis of the determination. The model use data acquiring unit 21 sets the generated information about musical pieces of a time series as the type estimation time series information. In addition, the model use data acquiring unit 21 adds information indicating that there is no musical piece that has been sung described above in front of the generated information about musical pieces of a time series and sets resultant information as recommendation time series information. The information indicating that there is no musical piece that has been sung is used for determining information to recommend using the musical piece recommendation model in a state in which no sing has been sung by the user. In addition, in a case in which information representing a musical piece has not been transmitted from the terminal 30, the recommendation time series information is formed only from the information indicating that there is no musical piece that has been sung, and the type estimation time series information is assumed to be absent. The model use data acquiring unit 21 sets each piece of the information described above as information used for recommendation to a user relating to the session.

The model use data acquiring unit 21 outputs the recommendation population information, the recommendation time series information, and the type estimation time series information that have been acquired to the model using unit 22.

The model using unit 22 is a functional unit that determines information about a musical piece to recommend to a user using the musical piece recommendation model and the type estimation model. The model using unit 22 determines information to recommend by inputting information based on the recommendation population information acquired by the model use data acquiring unit 21 to the musical piece recommendation model. The model using unit 22 determines information to recommend by inputting information based on the recommendation time series information acquired by the model use data acquiring unit 21 to the musical piece recommendation model in units of musical pieces in order of the time series. The model using unit 22 estimates a type to which a user belongs by inputting information based on the type estimation time series information acquired by the model use data acquiring unit 21 to the type estimation model in units of musical pieces in order of the time series.

The model using unit 22 inputs and stores the musical piece recommendation model and the type estimation model generated by the model generation system 10 and uses the stored models for determining information about a musical piece to recommend to a user. The model using unit 22 receives the recommendation population information and the recommendation time series information (the type estimation time series information) from the model use data acquiring unit 21 as inputs.

The model using unit 22 uses the type estimation time series information as an input value for the type estimation model and acquires type information that is an output value from the type estimation model. When the type estimation time series information is set as an input value for the type estimation model, the information is input in units of musical pieces in order of the time series of the session. The type information that becomes an output value is a numerical value (vector) representing a degree with which the user belongs to each type. The type information that becomes an output value is acquired every time when the type estimation time series information is input to the type estimation model in units of musical pieces. In other words, the type information that becomes an output value is acquired for each musical piece relating to the type estimation time series information. The numerical values correspond to a result of estimation of a type to which a user belongs. In addition, in a case in which information representing a musical piece has not been transmitted from the terminal 30, no type estimation time series information is present, and thus estimation of a type is not performed.

The model using unit 22, as illustrated in FIG. 13, uses the recommendation population information (the population information illustrated in FIG. 13), the recommendation time series information (the time series information of musical pieces illustrated in FIG. 13), and the type information (the type information illustrated in FIG. 13) acquired from the type estimation model as input values for the musical piece recommendation model and acquires recommendation information that is an output value from the musical piece recommendation model. When the recommendation time series information and the type information are set as input values for the type estimation model, the input is performed in units of musical pieces in order of the time series of the session. In addition, no type information corresponding to information, which indicates that no musical piece that has been sung is present, in the recommendation time series information, and thus for information indicating that no musical piece that has been sung is present, information representing that the type is none of the types is used.

The recommendation information that becomes an output value is a numerical value representing a degree of recommendation for each musical piece and a numerical value (vector) representing a degree of recommendation for each singer. The recommendation information that becomes an output value is acquired every time when the recommendation time series information is input to the musical piece recommendation model in units of musical pieces. In other words, the recommendation information that becomes an output value is acquired for each musical piece relating to the recommendation time series information (including a case in which no musical piece is present).

The model using unit 22 determines information to recommend to a user on the basis of the output value. For example, the model using unit 22 determines that a musical piece and a singer having the largest numerical values are recommended to a user. Alternatively, the model using unit 22 determines that musical pieces and singers corresponding to a number set in advance in order of the largest to smallest numerical value are recommended to a user. The model using unit 22 performs the determination every time when new recommendation information is acquired, in other words, every time when information representing a new musical piece as a sung musical piece is transmitted from the terminal 30. The model using unit 22 transmits the determined information to the terminal 30. The terminal 30 receives the information about recommendation transmitted from the recommendation server 1 and performs output such as display. The user can determine a musical piece to sing next by referring to the display.

For example, the processes performed by the model use data acquiring unit 21 and the model using unit 22 are performed as real time processing according to reception of information from the terminal 30 as described above. The function of the model using system 20 according to this embodiment has been described as above.

Figure 14:
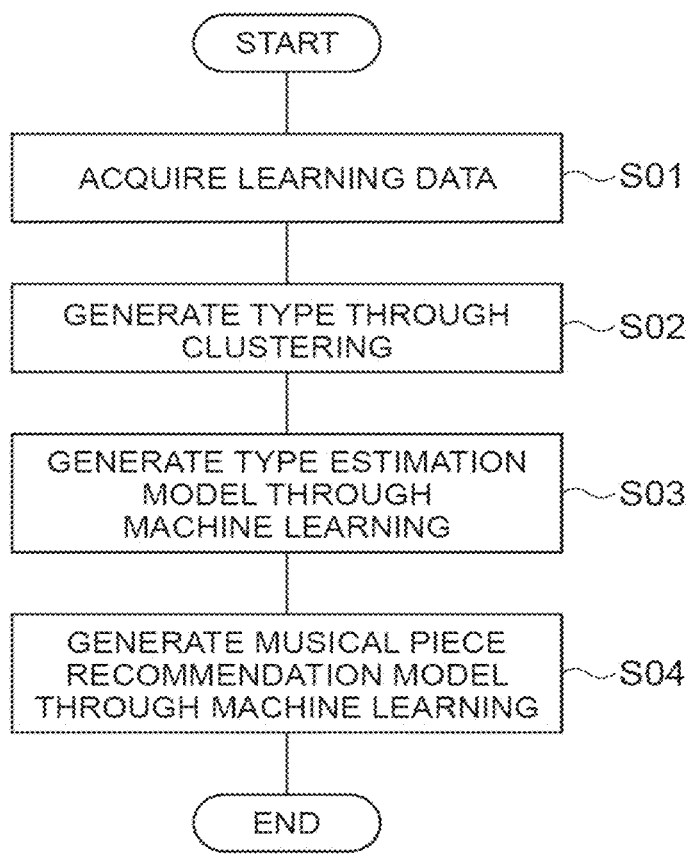
FIG. 14 is a flowchart illustrating a process performed when a musical piece recommendation model and a type estimation model are generated by a recommendation server that is a type estimation model generation system and a type estimation system according to an embodiment of the present invention.
Figure 15:
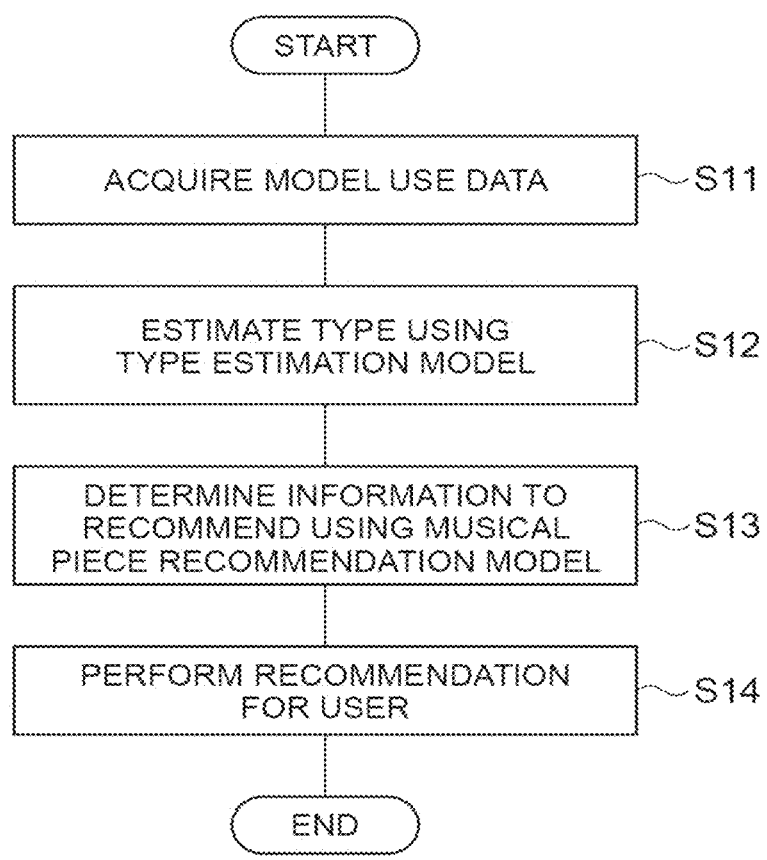
FIG. 15 is a flowchart illustrating a process performed when recommendation of a musical piece to a user is performed by a recommendation server that is a type estimation model generation system and a type estimation system according to an embodiment of the present invention.

Subsequently, the process performed by the recommendation server 1 according to this embodiment (an operation method performed by the recommendation server 1) will be described with reference to flowcharts illustrated in FIGS. 14 and 15. First, a process performed when a musical piece recommendation model and a type estimation model are generated, in other words, a process performed by the model generation system 10 according to this embodiment will be described with reference to the flowchart illustrated in FIG. 14.

In this process, learning data used for machine learning generating a musical piece recommendation model and learning data used for machine learning generating a type estimation model are acquired by the learning data acquiring unit 11 (S01). Subsequently, a plurality of types are generated by performing clustering of the learning time series information in the learning data acquired by the learning data acquiring unit 11, and learning type information based on the generated types is acquired (S02). Subsequently, a type estimation model is generated by the model generating unit 12 by performing machine learning on the basis of the learning time series information and the learning type information in the learning data (S03). At the time of this machine learning, information based on the learning time series information is set as an input to the type estimation model, and information based on the learning type information is set as an output of the type estimation model. The information based on the learning time series information is set as an input to the type estimation model in units of musical pieces in order of the time series.

Subsequently, a musical piece recommendation model is generated by the model generating unit 12 by performing machine learning on the basis of the learning time series information, the learning population information, the learning type information, and the learning use musical piece information in the learning data (S04). At the time of this machine learning, information based on the learning time series information, the learning population information, and the learning type information is set as an input to the musical piece recommendation model, and information based on the learning use musical piece information is set as an output of the musical piece recommendation model. The information based on the learning time series information is input to the musical piece recommendation model in units of musical pieces in order of the time series. The process performed when the musical piece recommendation model and the type estimation model are generated has been described as above.

Subsequently, a process performed when recommendation relating to a musical piece to a user is performed, in other words, a process performed by the model using system 20 according to this embodiment will be described with reference to a flowchart illustrated in FIG. 15. In this process, first, model use data used for the musical piece recommendation model and model use data used for the type estimation model are acquired by the model use data acquiring unit 21 (S11). The model use data is acquired using reception of a request for a recommended content transmitted from the terminal 30 as a trigger.

Subsequently, a type to which a user who is a recommendation target belongs is estimated by the model using unit 22 inputting information based on the type estimation time series information in the model use data to the type estimation model (S12). The information based on the type estimation time series information is input to the type estimation model in units of musical pieces in order of the time series. As a result of the estimation, type information that is an output value from the type estimation model is acquired.

Subsequently, recommendation information relating to a musical piece to recommend to a user is determined by the model using unit 22 inputting the information based on the recommendation population information, the information based on the recommendation time series information, and the type information in the model use data to the musical piece recommendation model (S13). Information based on the information based on the recommendation time series information is input to the musical piece recommendation model in units of musical pieces in order of the time series. Subsequently, recommendation of a musical piece to the user is performed on the basis of the recommendation time series information by the model using unit 22 (S14). The user can determine a musical piece to sing next by referring to the recommended information.

At a time point at which a request for a recommended content is received before a first musical piece is sung, no time series information that is information of a time series about a plurality of used musical pieces is present, and thus the time series information is not used in the process described above. In this case, the estimation of a type (S12) is not performed. The process performed when recommendation of a musical piece to a user is performed has been described as above.

According to this embodiment, a type of a user can be estimated by using the time series information that is information of a time series about a plurality of musical pieces used by the user who is an estimation target of the type on the basis of the type estimation model generated using machine learning. The information based on the time series information is input to the type estimation model in units of musical pieces in order of the time series, and thus estimation of a type with the sequence of musical pieces that have been sung taken into account can be performed. Thus, according to this embodiment, classification of types of users based on used musical pieces can be appropriately performed. For example, also for a user group of which the number of persons, an age group, sex, relation, and the like are not acquired, classification of types can be appropriately performed.

In addition, by performing recommendation using a type that is appropriately estimated, appropriate recommendation can be performed. Here, the estimation of a type of a user may be performed for a purpose other than the recommendation.

In addition, as in this embodiment, the time series information that is information of a time series about a plurality of used musical pieces may include information about singers of musical pieces, information about genres of musical pieces, information about words included in lyrics of musical pieces, and information of audio data of musical pieces. By using such information, estimation of a type that is appropriate in accordance with singers, genres, lyrics, and audio data (for example, a melody or a feeling for listening) can be performed. In addition, the time series information may not include any one thereof. Furthermore, the time series information may include information about musical pieces other than those described above.

In addition, as in this embodiment, a type to be estimated may be generated by performing clustering of the learning time series information. According to such a configuration, types to be estimated can be appropriate. Here, the types may be set in advance.

In this embodiment, not only recommendation of a musical piece but also recommendation of a singer can be performed using the same musical piece recommendation model. However, recommendation of both of these does not necessarily need to be performed, but only one thereof may be recommended. In addition, any information relating to a musical piece other than that described above may be recommended.

In this embodiment, although the recommendation server 1 is configured to include the model generation system 10 and the model using system 20, the model generation system 10 and the model using system 20 may be implemented independently of each other.

In addition, each of the musical piece recommendation model and the type estimation model generated by the model generation system 10 is assumed to be used as a program module that is a part of artificial intelligence software. The musical piece recommendation model and the type estimation model are used in a computer including a CPU and a memory. More specifically, in accordance with an instruction from the musical piece recommendation model and the type estimation model stored in the memory, the CPU of the computer operates to input information to an input layer of a neural network, perform an arithmetic operation based on weighting coefficients and the like that have been learned in the neural network, and output a result from an output layer of the neural network.

Each block diagram used for description of the embodiment described above illustrates blocks in units of functions. Such functional blocks (component units) are realized by an arbitrary combination of at least one of hardware and software. In addition, a method for realizing each functional block is not particularly limited. In other words, each functional block may be realized by one device that is combined physically or logically or a plurality of devices by directly or indirectly (for example, using a wire, wirelessly, or the like) connecting two or more devices separated physically or logically. A functional block may be realized by combining software with one device or the plurality of devices described above.

As functions, there are deciding, determining, judging, computing, calculating, processing, deriving, inspecting, searching, checking, receiving, transmitting, outputting, accessing, solving, selecting, choosing, establishing, comparing, assuming, expecting, regarding, broadcasting, notifying, communicating, forwarding, configuring, reconfiguring, allocating, mapping, assigning, and the like, and the functions are not limited thereto. For example, a functional block (constituent unit) enabling transmitting is referred to as a transmitting unit or a transmitter. As described above, a method for realizing all the functions is not particularly limited.

Figure 16:
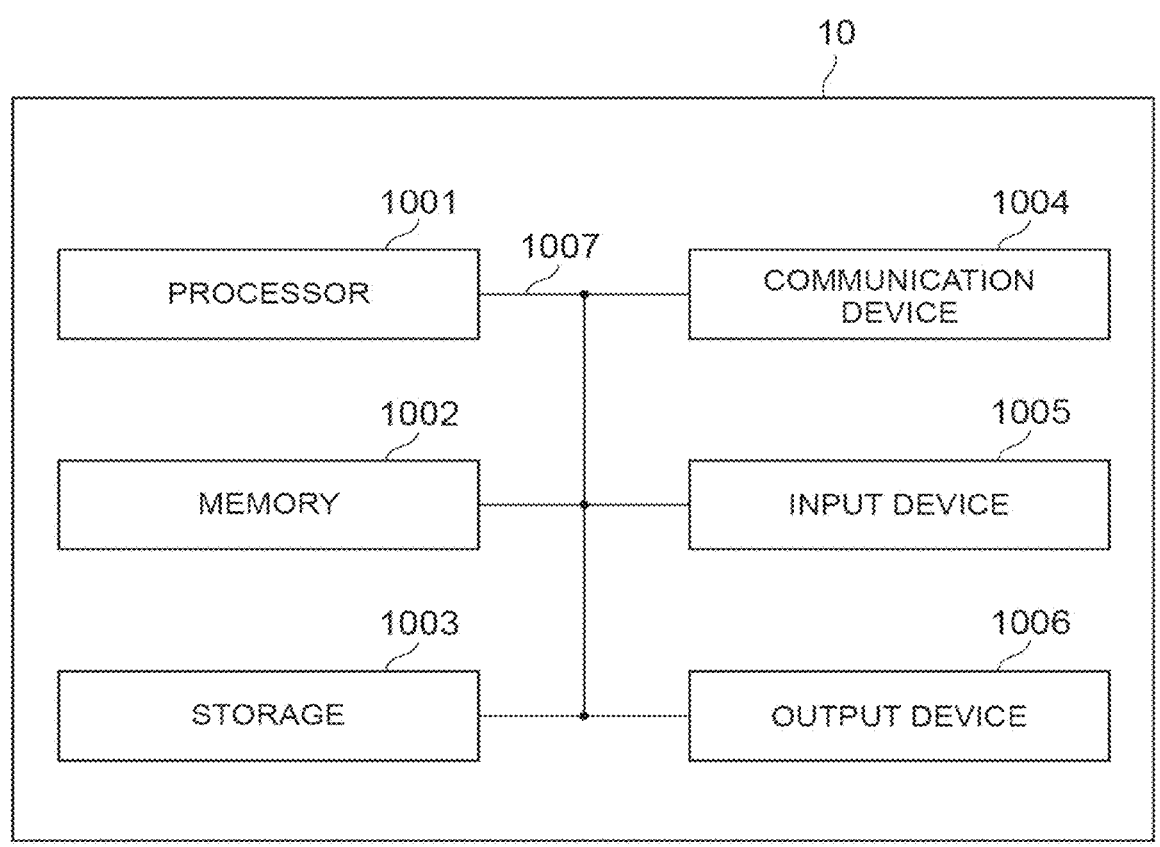
FIG. 16 is a diagram illustrating the hardware configuration of a recommendation server that is a type estimation model generation system and a type estimation system according to an embodiment of the present invention.

For example, the recommendation server 1 according to one embodiment of the present disclosure may function as a computer that performs information processing of the present disclosure. FIG. 16 is a diagram illustrating one example of the hardware configuration of the recommendation server 1 according to one embodiment of the present disclosure. The recommendation server 1 described above, physically, may be configured as a computer device including a processor 1001, a memory 1002, a storage 1003, a communication device 1004, an input device 1005, an output device 1006, a bus 1007, and the like. In addition, also the terminal 30 and the data server 40 may have a device configuration similar thereto.

In addition, in the following description, a term "device" may be rephrased as a circuit, a device, a unit, or the like. The hardware configuration of the recommendation server 1 may be configured to include one or a plurality of devices illustrated in the drawing and may be configured without including some of these devices.

Each function of the recommendation server 1 may be realized when the processor 1001 performs an arithmetic operation by causing predetermined software (a program) to be read onto hardware such as the processor 1001, the memory 1002, and the like, controls communication using the communication device 1004, and controls at least one of data reading and data writing for the memory 1002 and the storage 1003.

The processor 1001, for example, controls the entire computer by operating an operating system. The processor 1001 may be configured by a central processing unit (CPU) including an interface with peripheral devices, a control device, an arithmetic operation device, a register, and the like. For example, each function of the recommendation server 1 described above may be realized by the processor 1001.

In addition, the processor 1001 reads a program (program code), a software module, data, and the like from at least one of the storage 1003 and the communication device 1004 into the memory 1002 and executes various processes in accordance with these. As the program, a program causing a computer to execute at least some of the operations described in the embodiment described above is used. For example, each function of the recommendation server 1 may be realized by a control program that is stored in the memory 1002 and operated by the processor 1001. Although the various processes described above have been described as being executed by one processor 1001, the processes may be executed simultaneously or sequentially by two or more processors 1001. The processor 1001 may be mounted using one or more chips. In addition, the program may be transmitted from a network through a telecommunication line.

The memory 1002 is a computer-readable recording medium and, for example, may be configured by at least one of a read only memory (ROM), an erasable programmable ROM (EPROM), an electrically erasable programmable ROM (EEPROM), a random access memory (RANI), and the like. The memory 1002 may be referred to as a register, a cache, a main memory (a main storage device), or the like. The memory 1002 can store a program (a program code), a software module, and the like executable for performing the information processing according to one embodiment of the present disclosure.

The storage 1003 is a computer-readable recording medium and, for example, may be configured by at least one of an optical disc such as a compact disc ROM (CD-ROM), a hard disk drive, a flexible disk, a magneto-optical disk (for example, a compact disc, a digital versatile disc, or a Blu-ray (registered trademark) disc), a smart card, a flash memory (for example, a card, a stick, or a key drive), a floppy (registered trademark) disk, a magnetic strip, and the like. The storage 1003 may be referred to as an auxiliary storage device. The storage medium included in the recommendation server 1, for example, may be a database including at least one of the memory 1002 and a storage 1003, a server, or any other appropriate medium.

The communication device 1004 is hardware (a transmission/reception device) for performing inter-computer communication through at least one of a wired network and a wireless network and, for example, may be called also a network device, a network controller, a network card, a communication module, or the like.

The input device 1005 is an input device (for example, a keyboard, a mouse, a microphone, a switch, buttons, a sensor, or the like) that accepts an input from the outside. The output device 1006 is an output device (for example, a display, a speaker, an LED lamp, or the like) that performs output to the outside. In addition, the input device 1005 and the output device 1006 may have an integrated configuration (for example, a touch panel).

In addition, devices such as the processor 1001, the memory 1002, and the like are connected using a bus 1007 for communication of information. The bus 1007 may be configured as a single bus or buses different between devices.

In addition, the recommendation server 1 may be configured to include hardware such as a microprocessor, a digital signal processor (DSP), an application specific integrated circuit (ASIC), a programmable logic device (PLD), a field programmable gate array (FPGA), or the like, and a part or the whole of each functional block may be realized by the hardware. For example, the processor 1001 may be mounted using at least one of such hardware components.

The processing sequence, the sequence, the flowchart, and the like of each aspect/embodiment described in the present disclosure may be changed in order as long as there is no contradiction. For example, in a method described in the present disclosure, elements of various steps are presented in an exemplary order, and the method is not limited to the presented specific order.

The input/output information and the like may be stored in a specific place (for example, a memory) or managed using a management table. The input/output information and the like may be overwritten, updated, or added to. The output information and the like may be deleted. The input information and the like may be transmitted to another device.

A judgment may be performed using a value ("0" or "1") represented by one bit, may be performed using a Boolean value (true or false), or may be performed using a comparison between numerical values (for example, a comparison with a predetermined value).

The aspects/embodiments described in the present disclosure may be individually used, used in combination, or be switched therebetween in accordance with execution. In addition, a notification of predetermined information (for example, a notification of being X) is not limited to being performed explicitly and may be performed implicitly (for example, a notification of the predetermined information is not performed).

As above, while the present disclosure has been described in detail, it is apparent to a person skilled in the art that the present disclosure is not limited to the embodiments described in the present disclosure. The present disclosure may be modified or changed without departing from the concept and the scope of the present disclosure set in accordance with the claims. Thus, the description presented in the present disclosure is for the purpose of exemplary description and does not have any limited meaning for the present disclosure.

It is apparent that software, regardless of whether it is called software, firmware, middleware, a microcode, a hardware description language, or any other name, may be widely interpreted to mean a command, a command set, a code, a code segment, a program code, a program, a subprogram, a software module, an application, a software application, a software package, a routine, a subroutine, an object, an executable file, an execution thread, an order, a function, and the like.

In addition, software, a command, information, and the like may be transmitted and received via a transmission medium. For example, in a case in which software is transmitted from a website, a server, or any other remote source using at least one of a wiring technology such as a coaxial cable, an optical fiber cable, a twisted pair, a digital subscriber line (DSL) or the like and a radio technology (infrared rays, microwaves, and the like), at least one of such a wiring technology and a radio technology is included in the definition of the transmission medium.

Terms such as "system" and "network" used in the present disclosure are interchangeably used.

In addition, information, a parameter, and the like described in the present disclosure may be represented using absolute values, relative values with respect to predetermined values, or other corresponding information.

At least one of a server and a client may be called a transmission device, a receiving device, a communication device, or the like. In addition, at least one of the server and the client may be a device mounted in a mobile body, a mobile body, or the like. The mobile body may be a riding object (for example, a car, an airplane, or the like), may be a mobile body that moves unmanned (for example, a drone, an automatic driving car, or the like), or may be a robot (a manned type or an unmanned type). In addition, at least one of the server and the client includes a device that does not necessarily move at the time of a communication operation. For example, at least one of the server and the client may be an Internet of Things (IoT) device such as a sensor.

In addition, a server in the present disclosure may be rephrased with a client terminal. For example, each form/embodiment of the present disclosure may be applied to a configuration acquired by substituting communication between a server and a client terminal with communication among a plurality of user terminals (for example, it may be referred to as Device-to-Device (D2D), Vehicle-to-Everything (V2X), or the like). In such a case, the function included in the server described above may be configured to be included in the client terminal.

Similarly, the client terminal in the present disclosure may be rephrased with a server. In such a case, the function included in the client terminal described above may be configured to be included in the server.

Terms such as "determining" used in the present disclosure may include various operations of various types. The "deciding" and "determining", for example, may include a case in which judging, calculating, computing, processing, deriving, investigating, looking up, search, and inquiry (for example, looking up a table, a database, or any other data structure), or ascertaining is regarded as "deciding" and "determining". In addition, "deciding" and "determining" may include a case in which receiving (for example, receiving information), transmitting (for example, transmitting information), input, output, or accessing (for example, accessing data in a memory) is regarded as "deciding: and "determining". Furthermore, "deciding" and "determining" may include a case in which resolving, selecting, choosing, establishing, comparing, or the like is regarded as "deciding" and "determining". In other words, "deciding" and "determining" includes a case in which a certain operation is regarded as "deciding" and "determining". In addition, "deciding (determining)" may be rephrased with "assuming", "expecting", "considering", and the like.

Terms such as "connected" or "coupled" or all the modifications thereof mean all the kinds of direct or indirect connection or coupling between two or more elements and may include presence of one or more intermediate elements between two elements that are mutually "connected" or "coupled". Coupling or connection between elements may be physical coupling or connection, logical coupling or connection, or a combination thereof. For example, "connection" may be rephrased with "access". When used in the present disclosure, two elements may be considered as being mutually "connected" or "coupled" by using one or more wires and at least one of a cable and a print electric connection and, as several non-limiting and non-comprehensive examples, by using electromagnetic energy such as electromagnetic energy having wavelengths in a radio frequency region, a microwave region, and a light (both visible light and non-visible light) region.

Description of "on the basis of" used in the present disclosure does not mean "only on the basis of" unless otherwise mentioned. In other words, description of "on the basis of" means both "only on the basis of" and "on the basis of at least."

In the present disclosure, in a case in which names such as "first", "second", and the like is used, referring to each element does not generally limit the amount or the order of such an element. Such names may be used in the present disclosure as a convenient way for distinguishing two or more elements from each other. Accordingly, referring to the first and second elements does not mean that only the two elements are employed therein or the first element should precede the second element in a certain form.

In a case in which "include," "including," and modifications thereof are used in the present disclosure, such terms are intended to be inclusive like a term "comprising." In addition, a term "or" used in the present disclosure is intended to be not an exclusive logical sum.

In the present disclosure, for example, in a case in which an article such as "a," "an," or "the" in English is added through a translation, the present disclosure may include a plural form of a noun following such an article.

In the present disclosure, a term "A and B are different" may means that "A and B are different from each other". In addition, the term may mean that "A and B are different from C". Terms "separated", "combined", and the like may be interpreted similar to "different".

REFERENCE SIGNS LIST

1 recommendation server
10 model generation system
11 learning data acquiring unit
12 model generating unit
20 model using system
21 model use data acquiring unit
22 model using unit
30 terminal
40 data server
1001 processor
1002 memory
1003 storage
1004 communication device
1005 input device
1006 output device
1007 bus

The invention claimed is:

1. A type estimation model generation system that generates a type estimation model used for estimating one of a plurality of types to which a user belongs, the type estimation model generation system comprising:
a memory which stores historical data of musical pieces used at a location, wherein the musical pieces used are associated with a time of use and are not associated with user information of a user which used the musical piece; and
circuitry configured to:
organize the historical data into sessions corresponding to units of respective users of the musical pieces used:
generate learning time series information that is learning data used for machine learning and that is information of a time series about a sequence of a plurality of used musical pieces used by a user in a respective session;
generate learning type information representing types to which users who have used the plurality of musical pieces in a respective session belong; and
generate the type estimation model by performing machine learning using information based on the learning time series information as an input for the type estimation model in units of musical pieces in order of the time series and information based on the learning type information as an output of the type estimation model.

2. The type estimation model generation system according to claim 1, wherein the circuitry acquires the learning time series information including information about singers of the used musical pieces.

3. The type estimation model generation system according to claim 2, wherein the circuitry acquires the learning time series information including information about genres of the used musical pieces.

4. The type estimation model generation system according to claim 1, wherein the circuitry acquires the learning time series information including information about genres of the used musical pieces.

5. The type estimation model generation system according to claim 1, wherein the circuitry acquires the learning time series information including information about words included in lyrics of the used musical pieces.

6. The type estimation model generation system according to claim 1, wherein the circuitry acquires the learning time series information including information about audio data of the used musical pieces.

7. The type estimation model generation system according to claim 1, wherein the circuitry acquires information that is information of a time series about the plurality of used musical pieces and that includes information representing times at which the musical pieces are used and generates the learning time series information and learning use musical piece information on the basis of the times.

8. The type estimation model generation system according to claim 1, wherein the circuitry acquires the learning time series information for each of a plurality of users, generates a plurality of types that are estimation targets by performing clustering of the acquired learning time series information, and acquires learning type information on the basis of the generated types.

9. A type estimation system that estimates a type to which a user belongs among a plurality of types using a type estimation model generated by the type estimation model generation system according to claim 1, the type estimation system comprising circuitry configured to:
   acquire type estimation time series information that is information of a time series about a plurality of used musical pieces; and
   estimate a type to which a user belongs by inputting information based on the type estimation time series information to the type estimation model in units of musical pieces in order of the time series.

\* \* \* \* \*